(12) United States Patent
Kohn et al.

(10) Patent No.: US 8,173,163 B2
(45) Date of Patent: May 8, 2012

(54) POLYMERIC DRUG DELIVERY COMPOSITIONS AND METHODS FOR TREATING OPHTHALMIC DISEASES

(75) Inventors: Joachim B. Kohn, Piscataway, NJ (US); Isaac John Khan, Bridgewater, NJ (US); Carmine P. Lovine, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 331 days.

(21) Appl. No.: 12/390,255

(22) Filed: Feb. 20, 2009

(65) Prior Publication Data
US 2009/0238858 A1   Sep. 24, 2009

Related U.S. Application Data

(60) Provisional application No. 61/030,457, filed on Feb. 21, 2008, provisional application No. 61/139,378, filed on Dec. 19, 2008.

(51) Int. Cl.
*A61K 9/14*   (2006.01)
(52) U.S. Cl. .................................................. 424/486
(58) Field of Classification Search .................. None
See application file for complete search history.

(56) References Cited

U.S. PATENT DOCUMENTS

| | | | |
|---|---|---|---|
| 6,120,491 A * | 9/2000 | Kohn et al. ................. | 604/502 |
| 2006/0034891 A1 | 2/2006 | Lawin et al. | |
| 2009/0092665 A1 * | 4/2009 | Mitra et al. ................. | 424/450 |

* cited by examiner

*Primary Examiner* — Bethany Barham
(74) *Attorney, Agent, or Firm* — Fox Rothschild LLP

(57) ABSTRACT

Degradable polymeric compositions containing water-insoluble drugs blended with copolymers of biocompatible diphenol compound monomer units with pendant carboxylic acid groups polymerized with biocompatible diphenol compound monomer units with pendant carboxylic acid ester groups and poly(alkylene oxide) blocks, wherein the molar fraction in the copolymer of biocompatible diphenol compound monomer units with pendant carboxylic acid groups and poly(alkylene oxide) blocks relative to the weight percentage of the drug in the composition is effective to provide pseudo-zero order release of the drug from the composition during the sustained-release phase of drug delivery under physiological conditions. Ocular treatment methods and manufacturing methods are also disclosed.

20 Claims, 7 Drawing Sheets

POLYMERIC DRUG DELIVERY COMPOSITIONS AND METHODS FOR TREATING OPHTHALMIC DISEASES

CROSS-REFERENCE TO RELATED APPLICATIONS

This application claims priority under 35 U.S.C. §119(e) to U.S. Provisional Application Ser. No. 61/139,378, filed Dec. 19, 2008 and U.S. Provisional Application Ser. No. 61/030,457, filed Feb. 21, 2008, the disclosures of both of which are incorporated herein by reference in their entirety.

BACKGROUND OF THE INVENTION

Zero-order controlled release dosage forms deliver a near-constant concentration of a drug to a patient's body over extended periods of time. This is often desirable for maximum biological effect in particular if a drug exerts its activity by binding and inhibiting a cellular target. In addition, such dosage forms allow for less frequent administration than would be necessary with conventional burst release dosage forms. Furthermore, and of particular importance for ocular and intra-ocular drug delivery the local release provides for high tissue levels in the ocular tissues while minimizing systemic exposure thus minimizing side effects of a drug. Finally, the less frequent administration and continued therapeutic effect increases patient comfort and compliance.

Kohn et al. in U.S. Pat. No. 5,658,995 teaches implants formed from copolymers of tyrosine-based polycarbonates and poly(alkylene oxide). U.S. Pat. No. 5,877,224 discloses polymer-based controlled release drug delivery implants. Kohn et al., U.S. Pat. No. 6,120,491 discloses implantable polymer-based controlled release peptide drug delivery devices formed from polymers derived from the amino acid L-tyrosine. Published U.S. Patent Application No. 2003013848 discloses pharmaceutical formulations for regulating the timed release of biologically active compounds based on a polymer matrix. The disclosures of all four publications are incorporated herein by reference in their entirety.

None of the disclosed publications describe polymer-based controlled release drug delivery implants for water-insoluble drugs providing zero-order drug release. The local delivery of sustained, therapeutically effective concentrations of a drug that is safe, well-tolerated, and suitable for long-term use is a major need within the ophthalmic disease treatment community.

U.S. Pat. No. 6,548,078 discloses methods for treating and/or preventing retinal diseases with sustained release corticosteroids. Complex, multi-layered devices are employed, such as the multi-layered devices disclosed by U.S. Pat. No. 5,378,475.

Simple drug-polymer blends providing pseudo-zero order release are uncommon. Pseudo-zero order release requires a delicate balance between diffusional slow-down and acceleration of the release rate by erosion. It is very difficult to find simple polymer-based formulations that show this behavior in a way that acceleration and deceleration exactly cancel each other over longer periods of time. Individual polymer systems that show such behavior are not predictive of the behavior of other polymer systems. Therefore, there remains a need for biocompatible drug-polymer blends suitable for ocular and intra-ocular drug delivery with pseudo-zero order release kinetics.

SUMMARY OF THE INVENTION

This need is met by the present invention. It has now been discovered that pseudo-zero order release can be obtained for water-insoluble drugs with certain polymers of biocompatible diphenol compounds, such as certain of the polymers of U.S. Pat. No. 6,120,491, for example, polycarbonates, polyarylates, and poly(alkylene oxide) block copolymers thereof that are homopolymers and copolymers of tyrosine-derived diphenol monomers having pendent carboxylic acid groups. The entire disclosure of U.S. Pat. No. 6,120,491 is incorporated herein by reference. In particular, it has now been discovered that for water-insoluble drugs blended with random block copolymers of diphenol compound monomer units and poly(alkylene oxide) blocks some of which contain diphenol monomer units with pendant free carboxylic acid groups, diffusional slow down with degradation release can be countered by selection of the molar quantity of free carboxylic acid monomers and poly(alkylene oxide) blocks in the polymer. As the molar fraction of these units increase, the degradation release rate goes up.

Therefore, according to one aspect of the present invention, a biocompatible degradable polymer composition is provided, in which a water-insoluble drug is blended with a copolymer of biocompatible diphenol compound monomer units with pendant carboxylic acid groups polymerized with biocompatible diphenol compound monomer units with pendant carboxylic acid ester groups, and poly(alkylene oxide) blocks, wherein the molar fraction in the copolymer of biocompatible diphenol compound monomer units with pendant carboxylic acid groups and polyalkylene oxide blocks relative to the weight percentage of the drug in the composition is effective to provide pseudo-zero order release of the drug from the composition during the sustained-release phase of drug delivery under physiological conditions.

For purposes of the present invention, biocompatible compounds are defined as compounds that do not produce toxic or otherwise injurious tissue responses upon contact, and that do not form degradation products following tissue contact that are toxic or otherwise injurious to tissue. According to one embodiment, the biocompatible diphenol compounds are the biocompatible diphenol compounds of U.S. Pat. No. 6,120,491, particularly the tyrosine-derived diphenol compounds and the desaminotyrosyl-derived diphenol compounds disclosed therein. According to another embodiment, the copolymer is a polymer of U.S. Pat. No. 6,120,491 containing from about 1 mol % to about 75 mol %, preferably from about 2 mol % to about 60 mol %, or more preferably from about 3 mol % to about 25 mol %, tyrosine-derived diphenol compound monomer units with pendant carboxylic acid groups, for example non-ester desaminotyrosyl-tyrosine free carboxylic acid (DT), from about 25 mol % to about 99 mol % tyrosine-derived diphenol compound monomer units with pendant carboxylic acid ester groups, for example desaminotyrosyl-tyrosine esters (DTR), and from about 1 mol % to about 40 mol %, preferably from about 2 mol % to about 30 mol %, more preferably from about 3 mol % to about 25 mol %, or more preferably from about 4 mol % to about 20 mol %, poly(alkylene oxide) copolymer blocks. In one embodiment, the poly(alkylene oxide) is polyethylene glycol (PEG). Shorthand designations used herein for specific terpolymers of the present invention include poly(DTR-co-y % DT-co-z % PEG carbonate)

According to one embodiment, the water-insoluble drug is selected from peptides, eicosanoids, anti-inflammatory drugs, autonomic drugs, biologics, gene therapy agents, anti-infectives, retinoids, RNAi, photo sensitizers, steroids, mixture drugs, immunomodulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists. According to a more specific embodiment, the water-insoluble drug is the cyclic peptide voclosporin. According to another embodiment, the water-insoluble drug is present in an amount from about 0.5 wt % to about 80 wt % of the composition.

According to one embodiment, the composition further contains one or more additional components to modulate pseudo-zero order release selected from poly(alkylene oxides), polyvinyl alcohols, polypyrrolidones, polyvinyl pyrrolidones, water soluble polyacrylates, polyacrylic acid, poly (hydroxymethyl methacrylate), poly(L-lactic acid), poly(lactic acid-co-glycolic acid), polyanhydrides, polycaprolactones, poly(ortho esters), polyphosphazines, polyphosphoesters, sorbitol, sorbitol derivatives, polysorbates, polysaccharides, porogens, antioxidants, plasticizers, penetration enhancers and surfactants.

According to another embodiment, the composition is fabricated as an ocular implant, punctal plug, contact lens, film, mucoadhesive formulation, an in-situ forming gel or film, ointment, gel, iontophoresis formulation, or suspension. According to another embodiment, the present invention also provides methods for treating ocular conditions in a patient in need thereof by contacting an eye of the patient with a biocompat-ible degradable polymer composition of the present invention. According to a specific embodiment, the water insoluble drug is the cyclic peptide voclosporin.

According to one embodiment, the polymer composition delivers the drug to the patient locally. According to another embodiment, the polymer composition delivers the drug to the patient systemically. The composition may administer the drug to the patient topically, periocularly or intravitreally. The composition may also be contacted with the patient's tear duct to deliver the drug.

According to another embodiment, the ocular condition subject to treatment according to the method of the present invention is selected from idiopathic uveitis, corneal transplantation, dry eye syndrome, age-related macular degeneration (AMD, wet and dry), diabetic eye conditions, blepharitis, glaucoma, ocular hypertension, post-operative eye pain and inflammation, posterior segment neovascularization (PSNV), proliferative vitreoretinopathy (PVR), cytomegalovirus retinitis (CMV), endophthalmitis, choroidal neovascular membranes (CNVM), vascular occlusive diseases, allergic eye disease, tumors, retinitis pigmentosa, eye infections, scleritis, ptosis, miosis, eye pain, mydriasis, neuralgia, aging (e.g. muscle relaxants and other aesthetic products), cicatrizing ocular surface diseases, ocular infections, inflammatory ocular diseases, ocular surface diseases, corneal diseases, retinal diseases, ocular manifestations of systemic diseases, hereditary eye conditions, ocular tumors and increased intraocular pressure.

The tyrosine-derived biocompatible polymers of the present invention have low glass transition temperatures that make possible the preparation of drug-polymer blends for drug delivery with heretofore unknown loading levels of temperature-sensitive drugs. Therefore, the present invention also provides methods for manufacturing a biocompatible degradable polymer composition by blending a water-insoluble drug with a random block copolymer containing tyrosine-derived diphenol compound monomer units with pendant carboxylic acid groups, tyrosine-derived diphenol compound monomer units with pendant carboxylic acid ester groups, and poly(alkylene oxide) copolymer blocks, and then forming a composition with the blend, wherein (i) the composition comprises a drug loading from about 0.5 wt % to about 80 wt % of the composition, and (ii) the mole percent of diphenol compound monomer units with pendant carboxylic acid groups, and poly(alkylene oxide) copolymer blocks in the polymer relative to the weight percentage of the drug in the composition is effective to provide an essentially zero-order release of the drug from the composition during a sustained-release phase of drug delivery under physiological conditions. The method of the present invention is particularly advantageous for the preparation of drug delivery compositions wherein the water-insoluble drug is a peptide.

Other features of the present invention will be pointed out in the following description and claims, which disclose the principles of the invention and the best modes which are presently contemplated for carrying them out.

DETAILED DESCRIPTION OF THE INVENTION

Figure 1:
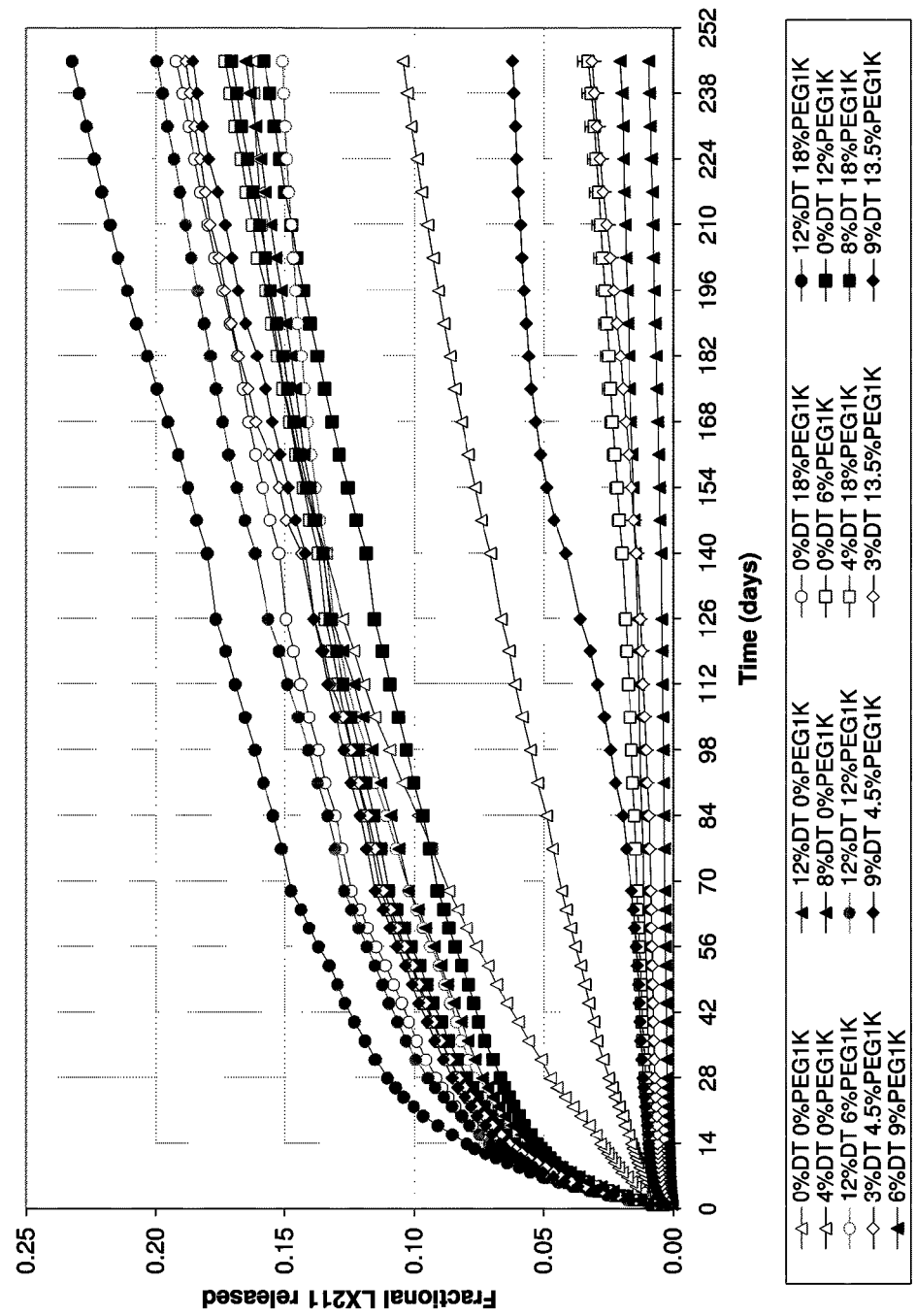
FIG. 1 is a graph showing the cumulative fractional release of voclosporin (ISA247 ("LX211"), Isotechnika, Inc., Alberta, Canada) (30% by weight) from 6 mm diameter×200-300 μm thick poly(DTE-co-y % DT-co-z % PEG1K carbonate) disks in phosphate buffered saline (pH 7.4) at 37° C.

The present invention provides a biocompatible degradable polymer composition, which includes a water-insoluble drug blended with a biocompatible diphenolic polymer, such as a polycarbonate or polyarylate. The biocompatible polymer is degradable under physiological conditions (e.g. pH 7.4 at 37° C.) and contains biocompatible diphenol compound monomer units with pendant carboxylic acid, biocompatible diphenol compound monomer units with pendant carboxylic acid ester groups, and poly(alkylene oxide) blocks. The molar fraction in the polymer of bio-compatible diphenol compound monomer units with pendant carboxylic acid groups and polyalkylene oxide blocks relative to the weight percentage of the drug in the composition is effective to provide pseudo-zero order release of the drug from the composition during the sustained-release phase of drug delivery under physiological conditions.

As used herein, the term "copolymer" refers to a non-homopolymer derived from two (2) or more (e.g. 2, 3, 4, 5, etc.) monomeric species. The term "terpolymer" refers to a non-homopolymer derived from exactly three (3) monomeric species.

According to one embodiment of the invention, the biocompatible polymer is a tyrosine-derived polycarbonate or polyarylate disclosed by U.S. Pat. No. 6,120,491. Examples of the polycarbonates and polyarylates of U.S. Pat. No. 6,120,491 providing pseudo-zero order release include polycarbonates and polyarylates with from about 1 mol % to about 75 mol %, preferably from about 2 mol % to about 60 mol %, or more preferably from about 3 mol % to about 25 mol %, tyrosine-derived diphenol compound monomer units with pendant carboxylic acid groups and from about 25 mol % to about 99 mol % tyrosine-derived diphenol compound monomer units with pendant carboxylic acid ester groups. The polycarbonate or polyarylate monomer derived units are random block copolymerized with a polyalkylene oxide so that the resulting polymer contains from about 1 mol % to about 40 mol %, preferably from about 2 mol % to about 30 mol %, more preferably from about 3 mol % to about 25 mol %, or more preferably from about 4 mol % to about 20 mol % poly(alkylene oxide) copolymer blocks and from about 60 mol % to about 99 mol % polycarbonate or polyarylate blocks.

Drug-polymer blends can exhibit multi-phasic drug release profiles, which typically include an initial burst of drug and a period of sustained drug release, the boundaries of which are readily identified by one of ordinary skill in the art. "Pseudo-zero order" release is a well-known term of art referring to a kinetic drug release profile equivalent to essentially zero order release obtained by balancing diffusional slow-down and acceleration of the release rate by erosion. For purposes of the present invention "essentially zero-order release" and "near zero-order release" refer to a drug release rate at or near zero order over the sustained release phase of drug delivery under physiological conditions. Compositions with drug release at or near zero order have drug release coefficients that are essentially unchanged relative to the arithmetic mean over the sustained release phase of drug delivery under physiological conditions.

For example, in one embodiment, "essentially zero-order release" and "near zero-order release" refer to the release kinetics of polymer compositions under physiological conditions, in which the release rate of drug from the composition varies by no more than ±10% over the sustained release phase following the initial burst for a period of about 1 week to about 4 years. One embodiment has a sustained release for a period between about one month to about three years. Additional embodiments include compositions in which the release rate of drug from the composition varies by no more than ±9%, ±7.5%, or ±5% over the sustained release phase following the initial burst.

As guided by the present specification, one of skill in the art can manipulate the release profile by adjusting certain features of the composition, for example, the polymer(s), drug(s), level of drug loading, surface area, etc. Furthermore, the initial burst can be shortened to less than one week by subsequent processing such as rinsing the blend to remove drug at or near the surface or by coating the composition with a bioerodible polymer that is either drug free or has a reduced drug content.

Preferably, the tyrosine-derived diphenol compound monomer units are copolymerized with a poly(alkylene oxide) and either a dicarboxylic acid or triphosgene so that the resulting polyarylate or polycarbonate random block copolymer contains from about 1 mol % to about 40 mol %, preferably from about 2 mol % to about 30 mol %, more preferably from about 3 mol % to about 25 mol %, or more preferably from about 4 mol % to about 20 mol % poly(alkylene oxide) derived blocks and from about 60 mol % to about 99 mol % polycarbonate or polyarylate blocks. In general, as the molecular weight of the poly(alkylene oxide) increases the amount in the copolymer decreases. Preferred polymers (see Formula I) include species of the polymers disclosed in U.S. Pat. No. 6,120,491, the contents of which is hereby incorporated by reference in its entirety.

Formula I:

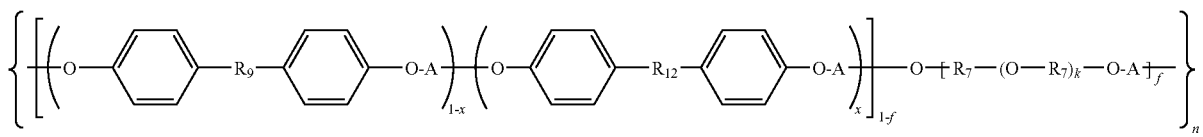

In Formula I, x and f are the molar ratios of the various subunits, with 0.25<X<0.99 and 0.01<f<0.40 being examples of polymers providing pseudo-zero order release. It is understood that the presentation of Formula I is schematic and that the polymer structure presented by Formula I is a true random copolymer where the different subunits can occur in any random sequence throughout the polymer backbone. Formula I provides a general chemical description of polycarbonates when A is

and of polyarylates when A is

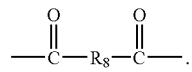

$R_8$ is selected from saturated and unsaturated, substituted and unsubstituted alkyl, alkylene oxide, aryl and alkylaryl groups containing up to 18 carbon atoms. Each occurrence of $R_7$ within each alkylene oxide block and throughout the polymer is independently an alkylene group containing up to 4 carbons, and k is between and 5 and 3,000. $R_9$ is an alkyl, aryl or alkylaryl group with up to 18 carbons with the specific proviso that this group contains as part of its structure a carboxylic acid group. $R_9$ can also contain non-carbon atoms such as nitrogen and oxygen. In particular, $R_9$ can have a structure related to derivatives of the natural amino acid tyrosine, cinnamic acid, or 3-(4-hydroxyphenyl)propionic acid. In these cases, $R_9$ assumes the specific structures shown in Formulae II and III:

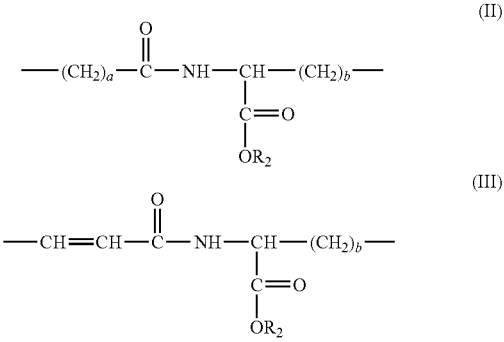

The indicators a and b in Formulae II and III can be independently 0, 1, or 2. $R_2$ is hydrogen.

$R_{12}$ is an alkyl, aryl or alkylaryl group substituted with a carboxylic acid ester group, wherein the ester is selected from straight and branched alkyl, alkylene oxide and alkylaryl esters containing up to 18 carbon atoms. $R_{12}$ can also contain non-carbon atoms such as nitrogen and oxygen. In particular, $R_{12}$ can have a structure related to derivatives of the natural amino acid tyrosine, cinnamic acid, or 3-(4-hydroxyphenyl) propionic acid. For derivatives of tyrosine, 3-(4-hydroxyphenyl) propionic acid, and cinnamic acid, $R_{12}$ assumes the specific structures shown in Formulae V and VI:

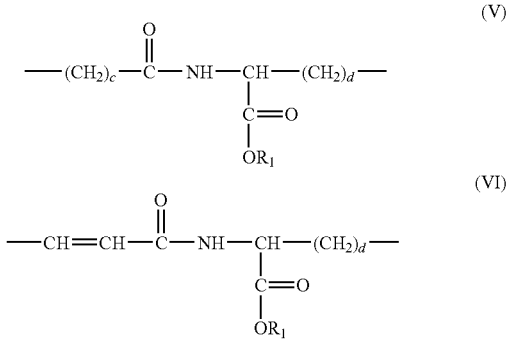

The indicators c and d can be independently 0, 1 or 2. $R_1$ is selected from straight and branched alkyl and alkylaryl groups containing up to 18 carbon atoms.

Methods for preparing the diphenol monomers are disclosed in commonly owned U.S. Pat. Nos. 5,587,507 and 5,670,602, the disclosures of both of which are hereby incorporated by reference. The preferred desaminotyrosyl-tyrosine esters are the methyl, ethyl, butyl, hexyl, octyl and benzyl esters. For purposes of the present invention, desaminotyrosyl-tyrosine methyl ester is referred to as DTM, desaminotyrosyl-tyrosine ethyl ester is referred to as DTE, desaminotyrosyl-tyrosyl-tyrosine benzyl ester is referred to as DTBn, desaminotyrosyl-tyrosine hexyl ester is referred to as DTH, desaminotyrosyl-tyrosine octyl ester is referred to as DTO, and the like. For purposes of the present invention, the desaminotyrosyl-tyrosine free acid is referred to as DT. Shorthand designations used herein for specific terpolymers include poly(DTE-co-y % DT-co-z % PEG carbonate) and poly(DTM-co-y % DT-co-z % $PEG_{1K}$ carbonate), wherein variables such as y and z refer to the mol % of the co-monomers in the polymer.

The random block copolymers of the present invention may be prepared by the method described by U.S. Pat. No. 5,658,995, the disclosure of which is also incorporated herein by reference. The monomeric units with free carboxylic acid groups are prepared as benzyl esters, wherein the benzyl esters are replaced by palladium catalyzed hydrogenation according to the method disclosed by U.S. Pat. No. 6,120,491, or as tert-butyl esters, where the tert-butyl groups are de-protected by the method disclosed by U.S. Patent Application Publication No. 20060034769, the disclosure of which is incorporated herein by reference.

The random block copolymers in accordance with the present invention have weight-average molecular weights between about 20,000 and about 400,000, and preferably about 100,000. The number-average molecular weights of the block copolymers are preferably above about 50,000. Molecular weight determinations are measured by GPC relative to polystyrene standards without further correction.

Additional biocompatible diphenol polymers suitable for use in the compositions of the present invention include, for example, the polycarbonates and polyarylates described in U.S. Patent Publication Nos. 20060034769 and 20050106119, the phosphorous-containing polymers of the '769 and '119 publications and U.S. Pat. Nos. 5,912,225 and 6,238,687, and the N-substituted polymers of International Application No. PCT/US07/81571, the contents of all of which are incorporated herein by reference in their entirety.

As used herein, depending upon the embodiment, the term "water-insoluble" refers to a substance that requires more than a certain amount of solvent for 1 part of solute. In one embodiment, the term "water-insoluble" refers to a substance that requires more than 10,000 parts of solvent for 1 part of solute. In another embodiment the term "water-insoluble" refers to a substance that requires more than 5,000 parts of solvent for 1 part of solute. In yet another embodiment, the term "water-insoluble" refers to a substance that requires more than 1,000 parts of solvent for 1 part of solute. In an additional embodiment, the term "water-insoluble" refers to a substance that requires more than 100 parts of solvent for 1 part of solute. The solvent includes water or aqueous solutions.

Suitable classes of water-insoluble drugs include peptides, eicosanoids (e.g. prostacyclins and prostaglandins), anti-inflammatory drugs, autonomic drugs (e.g. beta-blockers, alpha-blockers, beta-agonists, and alpha-agonists), biologics, gene therapy agents (e.g. viral vectors), anti-infectives (e.g antifungals, antibiotics, and antivirals), retinoids, RNAi, photo sensitizers, steroids, mixture drugs, immuno-modulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists. Preferably, the water-insoluble drug is a peptide. Exemplary peptides contain proteinogenic and non-proteinogenic amino acids. In one embodiment, the peptide is a cyclic peptide. A preferred cyclic peptide is voclosporin (ISA247, Isotechnika, Inc., Alberta, Canada). Voclosporin as an oral formulation is currently in Phase III development for the treatment of non-infectious, idiopathic uveitis. Preferably, the water-insoluble drug is present in an amount from about 0.5 wt % to about 80 wt % of the composition.

Optionally, the composition further includes up to about 70 wt %, and preferably between about 5 and about 50 wt %, of one or more additional components. Suitable additional components include polymers such as poly(alkylene oxides), polyvinyl alcohols, polypyrrolidones such as polyvinyl pyrrolidones, water soluble polyacrylates such as polyacrylic acid, poly(hydroxymethyl methacyrlate), and the like; biodegradable polymers and blends of biodegradable polymers selected from poly(L-lactic acid) (PLLA), poly(lactic acid-co-glycolic acid) (PLGA), polyanhydrides, polycaprolactones, poly(ortho esters), polyphosphazines and polyphosphoesters; sorbitol, sorbitol derivatives (e.g. SPAN) and polysorbates; porogens, antioxidants, plasticizers, penetration enhancers, other surfactants, and the like. Preferably, the optional additional component is selected from poly(alkylene oxides), sorbitol derivatives (e.g. SPAN), and polysorbates. A preferred poly(alkylene oxide) is polyethylene glycol (PEG). Preferred grades of PEG include PEG 1K to PEG 35K.

In an embodiment, a biocompatible degradable polymer drug delivery composition of the present disclosure comprises voclosporin blended with a terpolymer having the formula poly(DTR-co-y % DT-co-z % PEG carbonate), wherein y ranges from about 1 mol to about 75 mol, preferably from about 2 mol to about 60 mol, or more preferably from about 3 mol to about 25 mol and z ranges from about 1 mol to about 40 mol, preferably from about 2 mol to about 30 mol, more preferably from about 3 mol to about 25 mol, or more preferably from about 4 mol to about 20 mol. In an embodiment, the composition is further blended with an additional component, such as PLGA. In an embodiment, the addition of the PLGA to the composition results in a near-zero order in vitro release of voclosporin for at least two months.

The compositions of the present invention can be used to treat a condition for which essentially zero-order release of a drug from an implant is deemed appropriate. Suitable therapeutic forms include ocular implants for the treatment of conditions such as idiopathic uveitis, corneal transplantation, dry eye syndrome, age-related macular degeneration (AMD, wet and dry), diabetic eye conditions, blepharitis, glaucoma, ocular hypertension, post-operative eye pain and inflammation, posterior segment neovascularization (PSNV), proliferative vitreoretinopathy (PVR), cytomegalovirus retinitis (CMV), endophthalmitis, choroidal neovascular membranes (CNVM), vascular occlusive diseases, allergic eye disease, tumors, retinitis pigmentosa, eye infections, scleritis, ptosis, miosis, eye pain, mydriasis, neuralgia, aging (e.g. muscle relaxants and other aesthetic products), cicatrizing ocular surface diseases, ocular infections, inflammatory ocular diseases, ocular surface diseases, corneal diseases, retinal diseases, ocular manifestations of systemic diseases, hereditary eye conditions, ocular tumors, and increased intraocular pressure.

Treatment methods include both systemic and localized delivery of a drug to a patient in need thereof. Exemplary treatment forms include implants, punctal plugs, contact lenses, films, mucoadhesive formulations, in-situ forming gels/films (sol to gel, including but not limited to temperature, pH, and ion induced gelling), ointments, gels, iontophoresis formulations, and suspensions (e.g. injectable micro- and nano-particle solutions). Exemplary physical forms suitable for administering to a patient include tablets, rods, hollow rods, microspheres, nanospheres, fiber mats, fibers and films. In the case of ocular conditions, localized treatment includes contacting the eye with a composition of the present invention. For example any of the treatment forms mentioned above, which also contain a drug can be implanted into the eye tissue or applied directly to the surface of the patient's eye, i.e., topically, injected periocularly, or intravitreally inserted into ocular tissue. Systemic treatment methods include contacting a patient with a composition of the present invention in the vicinity of the eye so that the drug is delivered systemically to the eye for treatment of an ocular condition. Exemplary treatment forms for systemic administration include dermal patches, subcutaneous implants, gels, and ointments.

The compositions of the present invention can be readily adapted to other therapeutic forms to provide systemic or localized delivery of a drug in a patient. Other therapeutic forms include, for example, dermal patches, subcutaneous implants, ointments, and gels.

The compositions of the present invention can be fabricated into articles for drug delivery by any suitable method, including, for example, fiber spinning, electro-spinning, solvent casting, injection molding, thermoforming, extrusion, sheet extrusion, blown film extrusion, compression molding, and the like.

In one embodiment, the implants are prepared by simultaneously dissolving the polymer, drug, and, if present, optional component(s) in an organic solvent system capable of forming a homogenous solution of the polymer, drug, and optional component(s), solvent-casting the solution and then evaporating the solvent to leave behind a uniform, homogenous blend of polymer, drug and optional component(s). Typical solvent systems will include one or more solvents selected from methanol, methylene chloride, ethanol, ethylene glycol, glycerol, tetrahydrofuran, ethyl acetate, acetonitrile, acetone, diisopropyl ether, methyl t-butyl ether, chloroform, carbon tetrachloride, dichloroethane, and water. Individual drug and polymer components must possess solubility in at least one of the solvents of at least 1 g/l. The solvents may be pre-blended before the polymer drug, and optional component(s) are dissolved therein. Alternatively, the polymer drug, or optional component(s) may be dissolved in the individual solvent in which it is most soluble, after which the solutions are combined to form a solvent system in which the polymer drug, and optional component(s) are dissolved.

According to one embodiment, the polymer, drug, and optional component(s) should be dissolved in the mixing solvents at a level preferably between about 1 and about 30 percent by weight. According to another embodiment, the concentration is between about 5 and about 20 percent by weight. According to yet another embodiment, the concentration is between about 5 and about 10 percent by weight.

The relative solubilities of the polymer drug, and optional component(s) intended for use with the present invention in various organic solvents are well-known chemical properties. The selection of an organic solvent system in which a drug, a polymer, and an optional component(s) are forming a homogeneous solution at their respective concentrations may be readily determined without undue experimentation.

Briefly, using the known solubility profiles of each individual component, one would first consider a simple mixture of each of the individual solvents. For example, if the drug has some solubility in acetone, the polymer is soluble in methanol, and an optional component is soluble in methylene chloride, a mixture of acetone, methanol, and methylene chloride would be the initial starting point for the development of a solvent system that can dissolve all three of the components in a homogenous solution. Next, hydrogen bonding effects, polarity effects, and common solvent effects are considered. Inspection of the well-known solubility parameters (as listed in any comprehensive solvent information source such as the CRC Handbook of Physics and Chemistry) also assists in finding suitable solvent mixtures for all three solutes. The identification of complex solvent mixtures for different solutes is a well-known task in the formulation of numerous pharmaceutical and cosmetic products and can be readily accomplished by anyone skilled in the art.

Depending upon the solubility of the drug in the non-aqueous solvent, uniform, homogenous blends of drug, polymer and optional component(s) can be formed by co-precipitation. Known methods of precipitation that can be used include single emulsion (oil-in-water), double emulsion-solvent extraction (water-in-oil-in-water), oil-in-oil precipitation, water-in-oil-in-oil precipitation, anhydrous suspension (solid-oil-water or solid-oil-oil), coacervation, spray drying, etc. Precipitation methods will not be suitable when the drug is extremely soluble in organic solvents.

The drug-polymer matrices are dried to remove any residual solvent and are then fabricated by known methods (e.g, fiber spinning, electro-spinning, solvent casting, injection molding, thermoforming, etc.,) to produce a variety of useful articles. Depending on the thermal stability of the drug and the polymer, the articles can be shaped by conventional polymer-forming techniques such as extrusion, sheet extrusion, blown film extrusion, compression molding, injection molding, thermoforming, spray drying, injectable particle or microsphere suspension, and the like to form drug delivery devices.

Also presented are methods for treating an ocular condition in a patient in need thereof by contacting an eye of the patient with a composition of the present invention. Exemplary drugs and ocular conditions are mentioned above. The methods include delivering a drug to a patient locally or systemically. Exemplary techniques for contacting the patient's eye include contacting the patient's tear duct and/or administering the composition topically, periocularly, or intravitreally.

Also presented is a method of manufacturing a biocompatible degradable polymer composition (a) blending a water-insoluble drug with a polymer, which includes tyrosine-derived diphenol compound monomer units with pendant carboxylic acid groups, tyrosine-derived diphenol compound monomer units with pendant carboxylic acid ester groups, and poly(alkylene oxide) copolymer blocks, and (b) forming a drug delivery article with the blend, wherein (i) the composition includes a drug loading from about 0.5 wt % to about 80 wt % of the composition, and (ii) the mole percent of each monomer unit in the polymer relative to the weight percentage of the drug in the composition is effective to provide an essentially zero-order release of the drug from the composition during a sustained-release phase of drug delivery under physiological conditions. In one embodiment, the drug loading is from about 15 wt % to about 75 wt %. In another embodiment the drug loading is from about 30 wt % to about 50 wt %. The low glass transition temperature ($T_g$) of the polymers used in manufacturing the composition permits thermal processing (e.g. extrusion and other techniques listed above) of compositions having high drug loadings (e.g. from about 15 wt % to about 80 wt % of the composition).

The following non-limiting examples set forth herein below illustrate certain aspects of the invention.

EXAMPLES

Example 1

Solvent Casting 50 mg of poly(DTH suberate) and 22 mg of voclosporin were dissolved in 1 ml methylene chloride. The solution was cast in a Teflon dish and the solvent was evaporated overnight at room temperature. The semi-dried film was placed into a vacuum oven at 40° C. for a minimum of 48 hours. Disks of approximately 6 mm were punched from the dry film and weighed prior to testing.

Example 2

Compression Molding

Test samples were prepared by dissolving [a] grams [polymer] and [b] grams voclosporin in [c] ml methylene chloride using amounts set forth in Table I.

TABLE I

| [polymer] | [a] (grams) | [b] (grams) | [c] (ml) | [deg Celcius] |
| --- | --- | --- | --- | --- |
| p(DTE carbonate) | 2.00 | 0.86 | 15 | 130 |
| p(DTE-co-12% DT carbonate) | 2.03 | 0.87 | 15 | 130 |
| p(DTE-co-18% PEG1K carbonate) | 2.08 | 0.89 | 15 | 60 |
| p(DTE-co-12% DT-co-18% PEG1K carbonate) | 1.73 | 0.74 | 15 | 60 |
| p(DTE-co-4% DT carbonate) | 1.99 | 0.85 | 15 | 130 |
| p(DTE-co-8% DT carbonate) | 2.02 | 0.87 | 15 | 130 |
| p(DTE-co-6% PEG1K carbonate) | 2.06 | 0.88 | 15 | 100 |
| p(DTE-co-12% PEG1K carbonate) | 2.08 | 0.89 | 15 | 85 |
| p(DTE-co-12% DT-co-6% PEG1K carbonate) | 2.04 | 0.87 | 15 | 100 |
| p(DTE-co-12% DT-co-12% PEG1K carbonate) | 2.04 | 0.88 | 15 | 85 |
| p(DTE-co-4% DT-co-18% PEG1K carbonate) | 2.04 | 0.87 | 15 | 60 |
| p(DTE-co-8% DT-co-18% PEG1K carbonate) | 2.01 | 0.86 | 15 | 60 |
| p(DTE-co-3% DT-co-4.5% PEG1K carbonate) | 2.02 | 0.87 | 15 | 100 |
| p(DTE-co-9% DT-co-4.5% PEG1K carbonate) | 2.00 | 0.86 | 15 | 100 |
| p(DTE-co-3% DT-co-13.5% PEG1K carbonate) | 2.01 | 0.86 | 15 | 70 |
| p(DTE-co-9% DT-co-13.5% PEG1K carbonate) | 1.99 | 0.85 | 15 | 70 |
| p(DTE-co-6% DT-co-9% PEG1K carbonate) | 2.04 | 0.88 | 15 | 85 |

The solution was cast in a Teflon dish and the solvent was evaporated overnight at room temperature. The semi-dried film was placed into a vacuum oven at 40° C. for a minimum of 48 hours. The dry film was compression molded at [deg Celcius] (Table I) by pressing the drug-loaded polymer between stainless steel plates lined with parchment paper (to prevent sticking). Shims of 200 μm thick were used as spacers for controlling the final thickness of the sample. Total heat time was 10 minutes. Disks of approximately 6 mm were punched from the compression-molded film and weighed prior to testing.

Example 3

Kinetic Drug Release (KDR) Testing

A test sample as prepared in Example 2 was immersed in an initial phosphate buffered saline (PBS) with a pH of 7.4 at 37° C. At specified time intervals the sample was removed from the buffer solution and transferred to a fresh volume of PBS at 37° C. To the initial PBS solution, an equal volume of acetonitrile was added and the mixture was vigorously shaken. Aliquots of this mixture were analyzed using high performance liquid chromatography (HPLC) with an ultraviolet (UV) detector. Mobile phase A consisted of acetonitrile with 0.1% trifluoroacetic acid, and mobile phase B consisted of HPLC water with 0.1% trifluoroacetic acid. Analysis was run using a gradient of A and B starting at 50:50 mixture (by volume) and ending with 90:10 mixture (by volume). The area under the curve (AUC) for the released drug obtained from the relative peak intensity versus time was calculated by the HPLC software. The corresponding drug concentration was obtained from a standard curve, after adjustment for the acetonitrile dilution factor.

The cumulative fractional release of voclosporin from various polycarbonate formulations is shown in FIG. 1. There is a synergistic relationship between DT and relatively high levels of PEG to enhance drug release from the polymer, while drug retention in the polymer is correlated to the presence of DT in the absence of PEG.

Example 4

Polymer Erosion Testing

A test sample as prepared in Example 2 was immersed in an initial phosphate buffered saline (PBS) with a pH of 7.4 at 37° C. At specified time intervals the sample was removed from the buffer solution and transferred to a fresh volume of PBS at 37° C. To the initial PBS solution, 0.5N sodium hydroxide was added and the mixture was kept at room temperature for four hours. After four hours, 0.5N hydrochloric acid was added and the mixture was kept at room temperature for 30 minutes. The solution was frozen and lyophilized, then resuspended in acetonitrile:HPLC water:methanol (25:50:25, by volume) and filtered with a 0.45 micron Teflon filter prior to analysis. Aliquots of this mixture were analyzed using high performance liquid chromatography (HPLC) with an ultraviolet (UV) detector and evaporative light scattering detector. Mobile phase A consisted of acetonitrile with 0.1% trifluoroacetic acid, and mobile phase B consisted of HPLC water with 0.1% trifluoroacetic acid. Analysis was run using a gradient of A and B starting at 50:50 mixture (by volume) and ending with 90:10 mixture (by volume). The AUC for the dissolved monomers obtained from the relative peak intensity versus time was calculated by the HPLC software. The corresponding monomer concentration was obtained from a standard curve, after adjustment for the concentration factor. Erosion was calculated as the weight of the monomers dissolved in the buffer.

Figure 2:
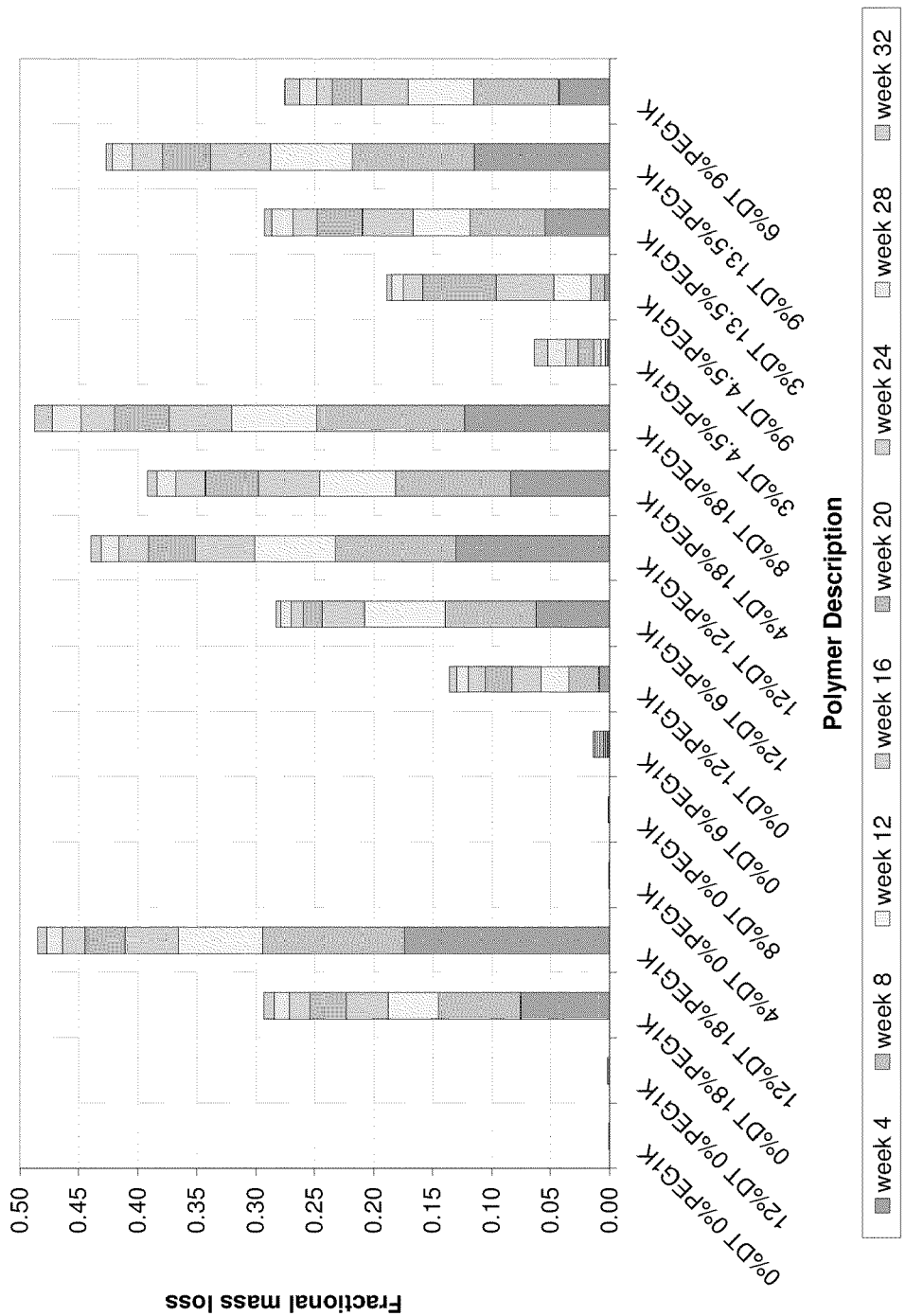
FIG. 2 is a graph showing the fractional mass loss (erosion) of poly(DTE-co-y % DT-co-z % PEG1K carbonate) 11 mm diameter×200-350 μm thick disks containing voclosporin (30% by weight) in phosphate buffered saline (pH 7.4) at 37° C.

Erosion (fractional mass loss) profiles of several polycarbonate disks containing voclosporin are shown in FIG. 2. Polymers having relatively high levels of PEG with or without DT show relatively high mass loss.

Example 5

Molecular Weight (Mw) Determination

A test sample as prepared in Example 2 was immersed in phosphate buffered saline (PBS) with a pH of 7.4 at 37° C. At specified time intervals samples were removed from the buffer solution, rinsed, and blotted dry. The dry sample was dissolved in dimethyl formamide with 0.1% trifluoroacetic acid. Aliquots of this mixture were analyzed using gel permeation chromatography (GPC) with a refractive index (RI) detector. Mobile phase was DMF with 0.1% trifluoroacetic acid. Retention time on the column was used to calculate the weight-average molecular weight (Mw) relative to a polystyrene standard. Loss in molecular weight of the polymer was calculated as the difference from its initial molecular weight.

Figure 3:
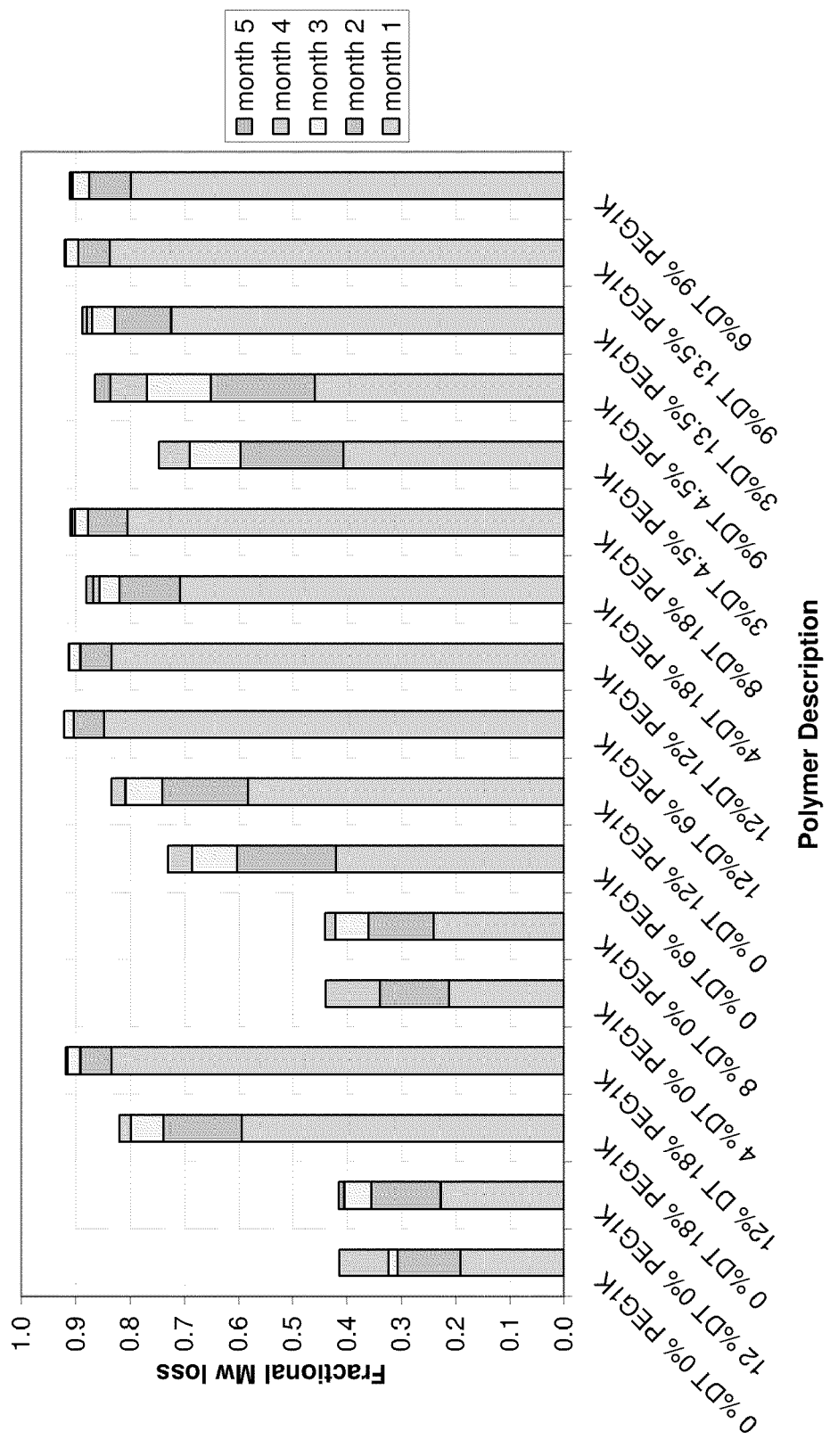
FIG. 3 is a graph showing the fractional molecular weight (Mw) loss for poly(DTE-co-y % DT-co-z % PEG1K carbonate) disks containing voclosporin (30% by weight) in phosphate buffered saline (pH 7.4) at 37° C.

Fractional molecular weight (Mw) loss of several polycarbonate disks containing voclosporin is shown in FIG. 3. Polymer compositions with DT and relatively high levels of PEG show the fastest decrease in molecular weight.

Example 6

Polyarylate Study

Figure 4:
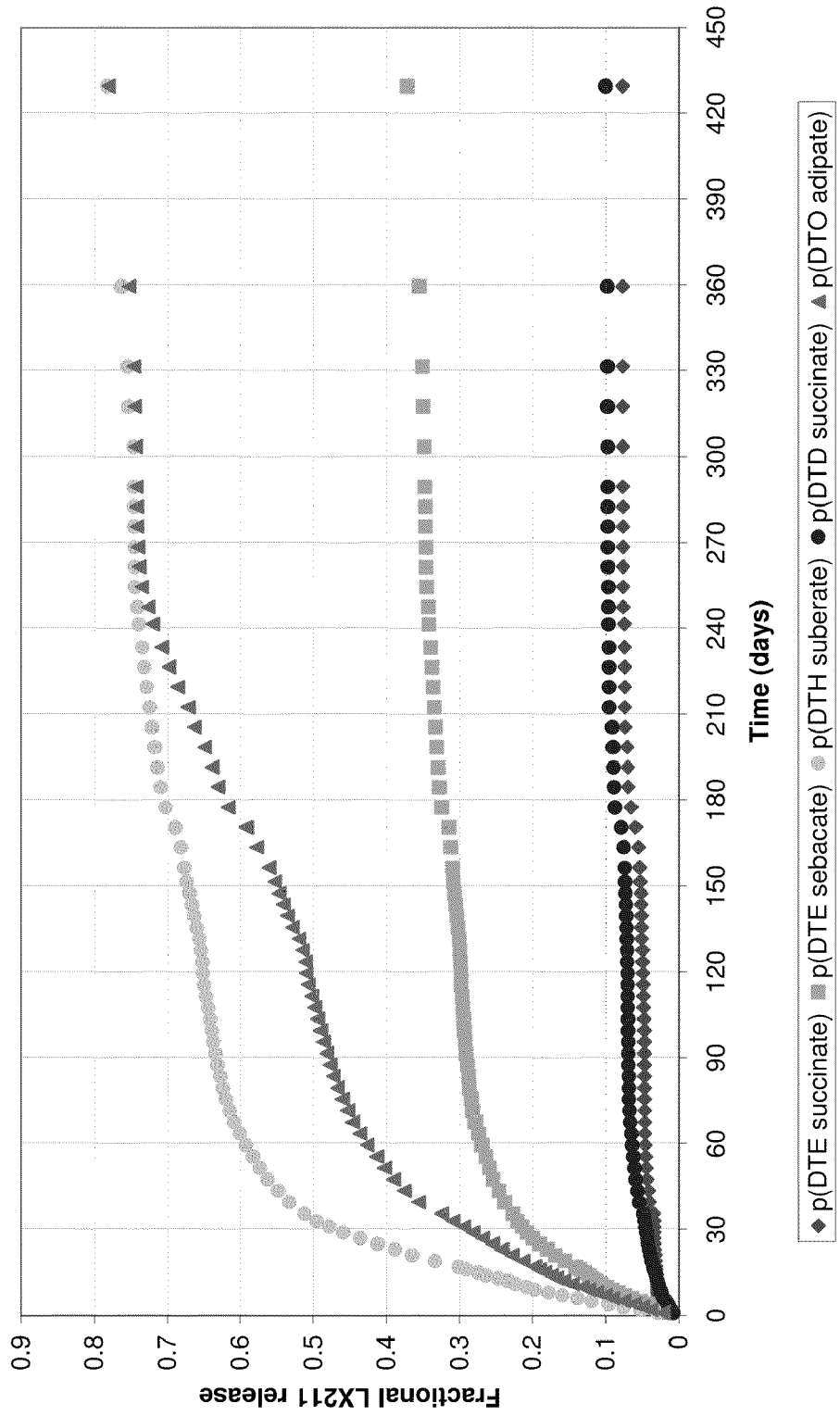
FIG. 4 is a graph showing the average cumulative fractional release of voclosporin ("LX211") (30% by weight) released from 6 mm diameter×50 μm thick polyarylate disks in phosphate buffered saline (pH 7.4) at 37° C.

Five base polyarylates were tested for kinetic drug release: poly(DTE sucinate), poly(DTE sebacate), poly(DTH suberate), poly(DTD succinate), and poly(DTO adipate) as in the previous examples. As shown in FIG. 4, the polyarylates exhibited biphasic release consisting of (a) an initial burst phase and (b) a sustained essentially zero order daily release. Based upon these results, one of skill in the art would expect carboxylated polyarylates, (e.g. poly(DTR diacid-co-y % DT diacid-co-z % PEG1K) or poly(DTR-co-y % DT-co-z % PEG1K diacid)) to exhibit a kinetic drug release profile, molecular weight degradation, and polymer erosion similar to that shown for the sub-family of poly(DTE-co-y % DT-co-z % PEG1K carbonate) terpolymers.

Example 7

Kinetic Drug Release (KDR) Testing of Poly(DTE-co-12% DT-co-24% PEG1K Carbonate)

Figure 5:
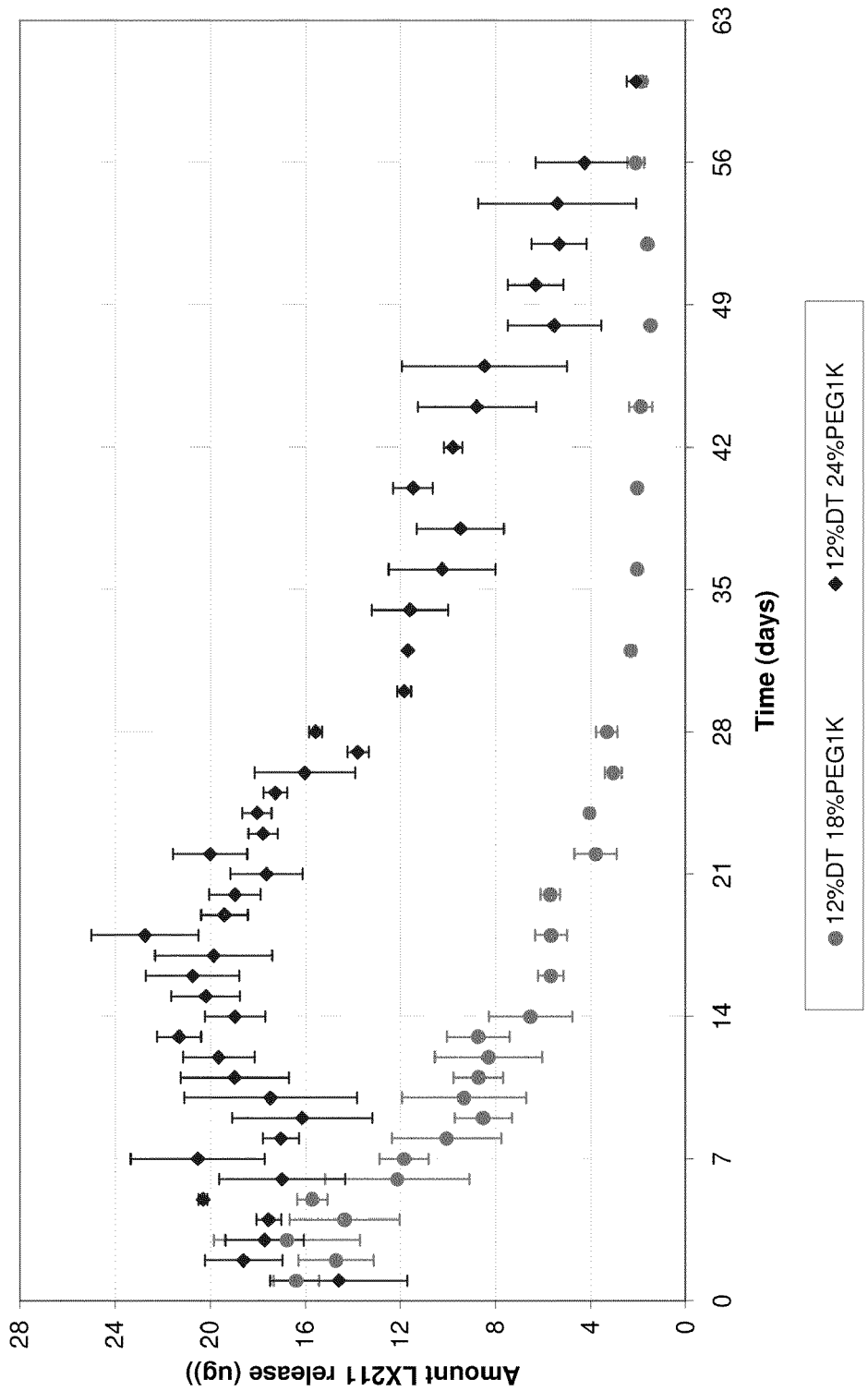
FIG. 5 is a graph showing the average daily release of voclosporin (30% by weight) from thin compression molded drug-loaded disks made from poly(DTE-co-12% DT-co-z % $PEG_{1K}$ carbonate), where z=18 and 24 mol %, in phosphate buffered saline at 37° C.

0.89 grams of poly(DTE-co-12% DT-co-24% $PEG_{1K}$ carbonate) and 0.38 grams of voclosporin were dissolved in 7.5 ml methylene chloride. The solution was cast in a Teflon dish and the solvent was evaporated overnight at room temperature. The semi-dried film was placed into a vacuum oven at 40° C. for a minimum of 48 hours. The dry film was compression molded at 60° C. by pressing the drug-loaded polymer between stainless steel plates lined with parchment paper (to prevent sticking). Shims of 200 µm thick were used as spacers for controlling the final thickness of the sample. Total heat time was 10 minutes. Disks of approximately 6 mm were punched from the compression molded film and weighed prior to testing. Testing of the kinetic drug release from this sample was similar to Example 3. The average daily release of the drug from the polymer matrix is shown in FIG. 5, which demonstrates how the daily drug release amount can be increased by increasing PEG content in the polycarbonate composition. Also plotted in FIG. 5 is the kinetic drug release from poly(DTE-co-12% DT-co-18% $PEG_{1K}$ carbonate) for comparison. Both samples have 30% (by weight) loading of voclosporin. An extended release of approximately 1 month was observed from the poly(DTE-co-12% DT-co-24% $PEG_{1K}$ carbonate) matrix.

Example 8

Compression Molding

Test samples were prepared by dissolving [a] grams [polymer] and [b] grams voclosporin in [c] ml methylene chloride using amounts set forth in Table II.

TABLE II

| [polymer] | [a] (grams) | [b] (grams) | [c] (ml) | [deg Celcius] |
|---|---|---|---|---|
| p(DTM-co-12% DT-co-18% PEG1K carbonate) | 4.00 | 0.71 | 60 | 70 |
| p(DTM-co-14% DT-co-20% PEG1K carbonate) | 4.00 | 0.71 | 60 | 80 |
| p(DTM-co-12% DT-co-24% PEG1K carbonate) | 4.06 | 0.72 | 80 | 80 |

The solution was cast in a Teflon dish and the solvent was evaporated overnight at room temperature. The semi-dried film was dried under nitrogen at room temperature for approximately 48 hours. The dry film was compression molded at [deg Celcius] (Table II) by pressing the drug-loaded polymer between stainless steel plates lined with parchment paper (to prevent sticking). Shims of 360 μm thick were used as spacers for controlling the final thickness of the sample. Total heat time was 5 minutes. Disks of approximately 6 mm were punched from the compression-molded film and weighed prior to testing.

Example 9

Kinetic Drug Release (KDR) Testing

Figure 6:
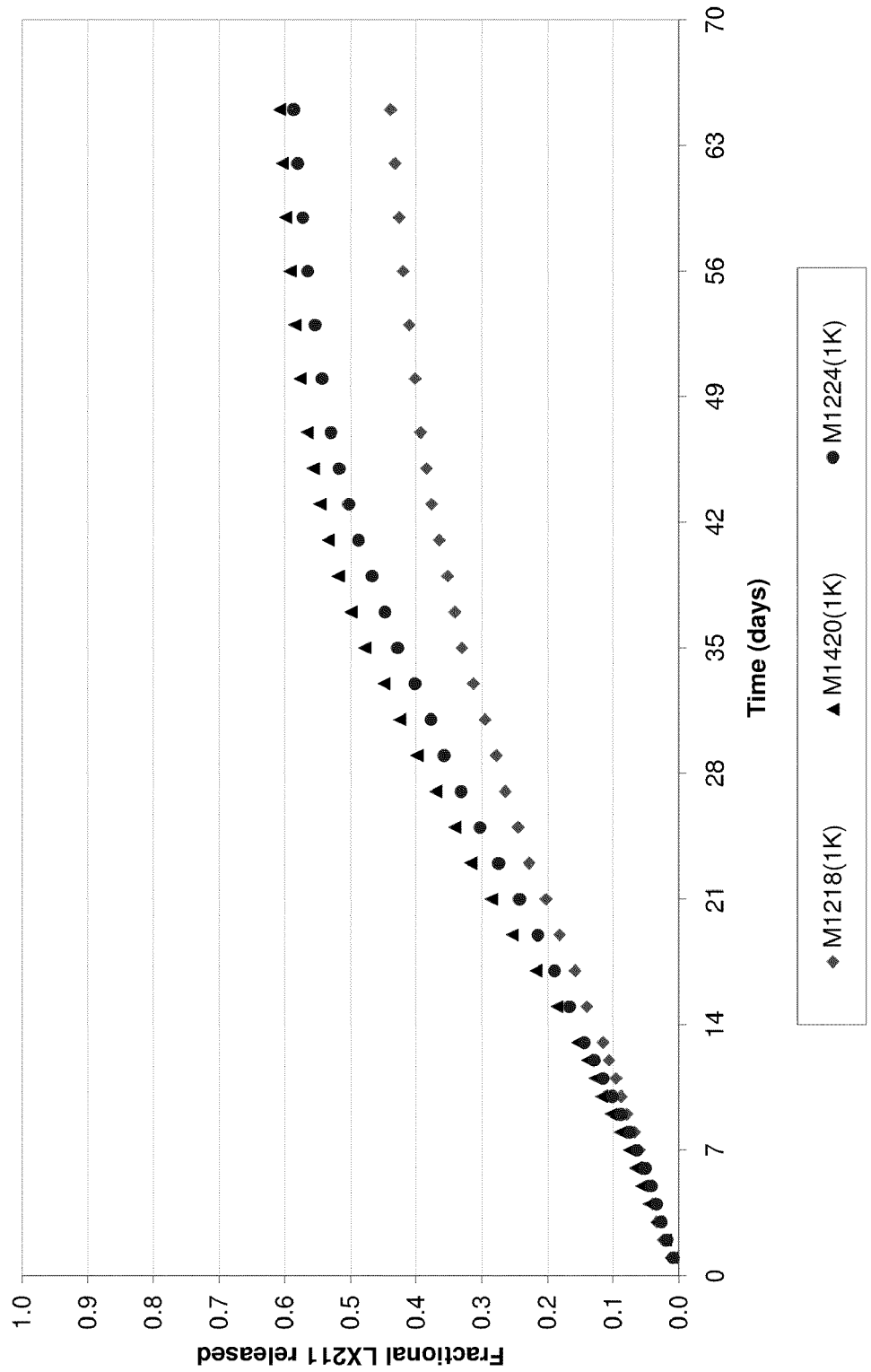
FIG. 6 is a graph showing the cumulative fractional release of voclosporin ("LX211") (15% by weight) released from 6 mm diameter×360 μm thick poly(DTM-co-y % DT-co-z % PEG1K carbonate) disks in phosphate buffered saline (pH 7.4) at 37° C.

A test sample as prepared in Example 8 was immersed in an initial phosphate buffered saline (PBS) with a pH of 7.4 at 37° C. At specified time intervals the sample was removed from the buffer solution and transferred to a fresh volume of PBS at 37° C. To the initial PBS solution, an equal volume of acetonitrile was added and the mixture was vigorously shaken. Aliquots of this mixture were analyzed using high performance liquid chromatography (HPLC) with an ultraviolet (UV) detector. Mobile phase A consisted of acetonitrile with 0.1% trifluoroacetic acid, and mobile phase B consisted of HPLC water with 0.1% trifluoroacetic acid. Analysis was run using a gradient of A and B starting at 70:30 mixture (by volume) and ending with 75:25 mixture (by volume). The area under the curve (AUC) for the released drug obtained from the relative peak intensity versus time was calculated by the HPLC software. The corresponding drug concentration was obtained from a standard curve, after adjustment for the acetonitrile dilution factor. The cumulative fractional release of voclosporin (voclosporine) from various polycarbonate formulations is shown in FIG. 6, which demonstrates how the cumulative drug release can be modulated by variation in polycarbonate polymer compositions containing DTM, DT, and PEG.

Example 10

Compression Molding

Test samples were prepared by dissolving 1.99 grams p(DTE-co-12% DT-co-24% PEG1K carbonate), 2.01 grams PLGA, and 0.70 grams voclosporin in 60 ml methylene chloride. The solution was cast in a Teflon dish and the solvent was evaporated overnight at room temperature. The semi-dried film was dried under nitrogen at room temperature for a approximately 48 hours. The dry film was compression molded at 80° C. by pressing the drug-loaded polymer between stainless steel plates lined with parchment paper (to prevent sticking). Shims of 360 μm thick were used as spacers for controlling the final thickness of the sample. Total heat time was 5 minutes. Disks of approximately 6 mm were punched from the compression-molded film and weighed prior to testing.

Example 11

Kinetic Drug Release (KDR) Testing

Figure 7:
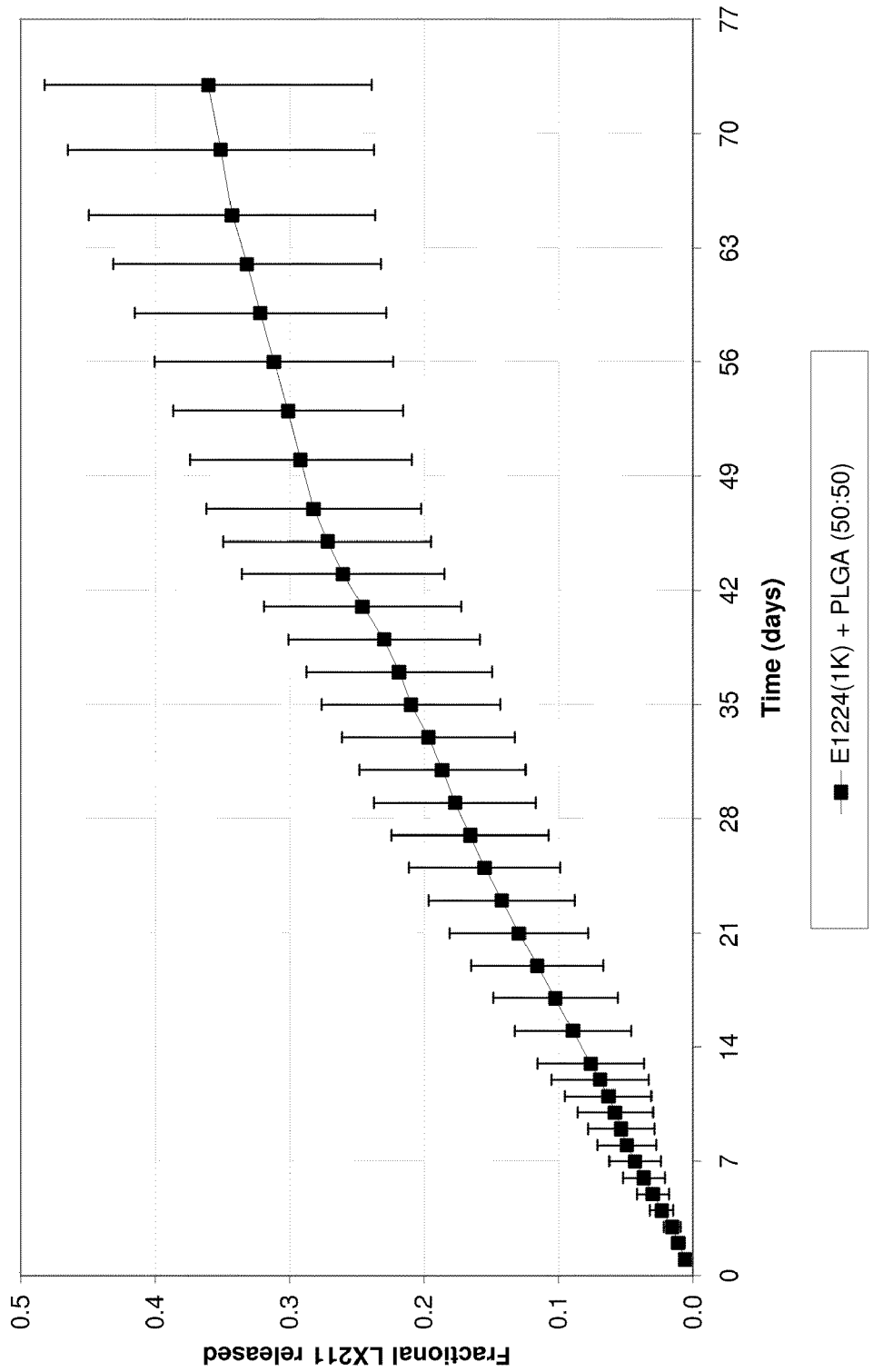
FIG. 7 is a graph showing the cumulative fractional release of voclosporin ("LX211") (15% by weight) released from 6 mm diameter×360 μm thick disks comprised of poly(DTE-co-12% DT-co-24% PEG1K carbonate) blended with 50:50 PLGA (blended 1:1, by weight) in phosphate buffered saline (pH 7.4) at 37° C.

A test sample as prepared in Example 10 was immersed in an initial phosphate buffered saline (PBS) with a pH of 7.4 at 37° C. At specified time intervals the sample was removed from the buffer solution and transferred to a fresh volume of PBS at 37° C. To the initial PBS solution, an equal volume of acetonitrile was added and the mixture was vigorously shaken. Aliquots of this mixture were analyzed using high performance liquid chromatography (HPLC) with an ultraviolet (UV) detector. Mobile phase A consisted of acetonitrile with 0.1% trifluoroacetic acid, and mobile phase B consisted of HPLC water with 0.1% trifluoroacetic acid. Analysis was run using a gradient of A and B starting at 70:30 mixture (by volume) and ending with 75:25 mixture (by volume). The area under the curve (AUC) for the released drug obtained from the relative peak intensity versus time was calculated by the HPLC software. The corresponding drug concentration was obtained from a standard curve, after adjustment for the acetonitrile dilution factor. The cumulative fractional release of voclosporin (voclosporine) from the polycarbonate-PLGA blended formulation is shown in FIG. 7, which demonstrates a near-zero order in vitro release of the drug voclosporin for over 2 months at body temperature. Each polymer in the blend tested separately does not show a near-zero order release over this time interval.

The description of the preferred embodiments should be taken as illustrating, rather than as limiting, the present invention as defined by the claims. As will be readily appreciated, numerous combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A degradable polymeric drug delivery composition comprising a water-insoluble drug blended with a copolymer comprising from 3 mol to 12 mol % biocompatible tyrosine-derived diphenol compound monomer units with pendant carboxylic acid groups polymerized with from 79 mol % to 91 mol % biocompatible tyrosine-derived diphenol compound monomer units with pendant carboxylic acid ester groups, and from 6 mol % to 18 mol % poly(alkylene oxide) blocks, wherein a molar fraction in the copolymer of biocompatible diphenol compound monomer units with pendant carboxylic acid groups and polyalkylene oxide blocks relative to a weight percentage of the water-insoluble drug in the composition is effective to provide pseudo-zero order release of the drug from the composition during a sustained-release phase of drug delivery under physiological conditions.

2. The composition of claim 1, wherein said water-insoluble drug is selected from the group consisting of peptides, cyclic peptides, eicosanoids, anti-inflammatory drugs, autonomic drugs, biologics, gene therapy agents, anti-infectives, retinoids, RNAi, photo sensitizers, steroids, mixture drugs, immunomodulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists.

3. The composition of claim 2, wherein said peptide is a macrolide or cyclic peptide.

4. The composition of claim 3, wherein said cyclic peptide is voclosporin.

5. The composition of claim 1, wherein said water-insoluble drug is present in an amount from about 0.5 wt % to about 80 wt % of the composition.

6. The composition of claim 1, further comprising one or more additional components selected from the group consisting of poly(alkylene oxides), polyvinyl alcohols, polypyrrolidones, polyvinyl pyrrolidones, water soluble polyacrylates, polyacrylic acid, poly(hydroxymethyl methacrylate), poly(L-lactic acid), poly(lactic acid-co-glycolic acid), polyanhydrides, polycaprolactones, poly(ortho esters), polyphosphazines, polyphosphoesters, sorbitol, sorbitol derivatives, polysorbates, polysaccharides, porogens, antioxidants, plasticizers, penetration enhancers and surfactants.

7. The composition of claim 6, wherein said additional component is a poly(lactic acid-co-glycolic acid).

8. The composition of claim 1, characterized by being fabricated as an ocular implant, punctal plug, contact lens, film, injectable particle or microsphere suspension, mucoadhesive formulation, an in-situ forming gel or film, gel, iontophoresis formulation, tablet, rod, hollow rod, microsphere, nanosphere, fiber mat, fiber, dermal patches, subcutaneous implant or ointment.

9. The composition of claim 1 wherein said tyrosine-derived diphenol compound monomer units with pendant carboxylic acid ester groups are desaminotyrosyl-tyrosine esters selected from the group consisting of methyl, ethyl, butyl, hexyl, octyl and benzyl esters.

10. A method for treating an ocular condition in a patient in need thereof comprising contacting an eye of the patient with a degradable polymeric drug delivery composition comprising a water-insoluble drug blended with a copolymer comprising from 3 mol % to 12 mol % biocompatible tyrosine-derived diphenol compound monomer units with pendant carboxylic acid groups polymerized with from 79 mol % to 91 mol % biocompatible tyrosine-derived diphenol compound monomer units with pendant carboxylic acid ester groups, and from 6 mol % to 18 mol poly(alkylene oxide) blocks, wherein a molar fraction in the copolymer of biocompatible tyrosine-derived diphenol compound monomer units with pendant carboxylic acid groups and polyalkylene oxide blocks relative to a weight percentage of the water-insoluble drug in the composition is effective to provide pseudo-zero order release of the drug from the composition during a sustained-release phase of drug delivery under physiological conditions.

11. The method of claim 10, wherein said water-insoluble drug is selected from the group consisting of peptides, cyclic peptides, eicosanoids, anti-inflammatory drugs, auto-nomic drugs, biologics, gene therapy agents, anti-infectives, retinoids, RNAi, photo sensitizers, steroids, mixture drugs, immunomodulators, chemotherapeutic agents, G-coupled protein receptor antagonists, receptor tyrosine kinase (RTK) inhibitors, growth hormone inhibitors, integrin inhibitors, Sdf1/CXCR4 pathway inhibitors, and nACh receptor antagonists.

12. The method of claim 10, wherein said water-insoluble drug is present in an amount from 0.5 wt % to about 80 wt % of the composition.

13. The method of claim 11, wherein said peptide is a macrolide or cyclic peptide.

14. The method of claim 13, wherein said cyclic peptide is voclosporin.

15. The method of claim 10, wherein said ocular condition is selected from the group consisting of idiopathic uveitis, corneal transplantation, dry eye syndrome, age-related macular degeneration (AMD, wet and dry), diabetic eye conditions, blepharitis, glaucoma, ocular hypertension, post-operative eye pain and inflammation, posterior segment neovascularization (PSNV), proliferative vitreoretinopathy (PVR), cytomegalovirus retinitis (CMV), endophthalmitis, choroidal neovascular membranes (CNVM), vascular occlusive diseases, allergic eye disease, tumors, retinitis pigmentosa, eye infections, scleritis, ptosis, miosis, eye pain, mydriasis, neuralgia, aging (e.g. muscle relaxants and other aesthetic products), cicatrizing ocular surface diseases, ocular infections, inflammatory ocular diseases, ocular surface diseases, corneal diseases, retinal diseases, ocular manifestations of systemic diseases, hereditary eye conditions, ocular tumors and increased intraocular pressure.

16. The method of claim 10, wherein said composition is fabricated as an ocular implant, punctal plug, contact lens, film, injectable particle or microsphere suspension, mucoadhesive formulation, an in-situ forming gel or film, gel, iontophoresis formulation, tablet, rod, hollow rod, microsphere, nanosphere, fiber mat, fiber, dermal patches, subcutaneous implant or ointment.

17. The method of claim 10 wherein said tyrosine-derived diphenol compound monomer units with pendant carboxylic acid ester groups are desaminotyrosyl-tyrosine esters selected from the group consisting of methyl, ethyl, butyl, hexyl, octyl and benzyl esters.

18. A method of manufacturing a degradable polymeric drug delivery composition comprising (a) blending a water-insoluble drug with a copolymer comprising from 3 mol % to 12 mol % tyrosine-derived diphenol compound monomer units with pendant carboxylic acid groups, from 79 mol % to 91 mol tyrosine-derived diphenol compound monomer units with pendant carboxylic acid ester groups, and from 6 mol % to 18 mol % poly(alkylene oxide) copolymer blocks, and (b) forming a drug delivery article with the blend, wherein (i) the composition comprises a drug loading from about 0.5 wt % to about 80 wt % of the composition, and (ii) a mole percent of diphenol compound monomer units with pendant carboxylic acid groups, and poly(alkylene oxide) copolymer blocks in said copolymer relative to a weight percentage of the drug in the composition is effective to provide an essentially zero-order release of the drug from the composition during a sustained-release phase of drug delivery under physiological conditions.

19. The method of claim 18, wherein said water-insoluble drug is a macrolide or cyclic peptide.

20. The method of claim 18, wherein said drug delivery article is formed into an ocular implant, punctal plug, contact lens, film, injectable particle or microsphere suspension, mucoadhesive formulation, an in-situ forming gel or film, ointment, gel or iontophoresis formulation, tablet, rod, hollow rod, microsphere, nanosphere, fiber mat, fiber, dermal patches, subcutaneous implant or ointment.

* * * * *